United States Patent
Wilkins et al.

(10) Patent No.: US 6,180,335 B1
(45) Date of Patent: Jan. 30, 2001

(54) APPARATUS FOR DETECTING CONTAMINATION IN FOOD PRODUCTS

(75) Inventors: Ebtisam S. Wilkins; Plamen B Atanassov; Dmitri M. Ivnitski; Ihab A. Abdel-Hamid, all of Albuquerque, NM (US)

(73) Assignee: University of New Mexico, Albuquerque, NM (US)

( * ) Notice: Under 35 U.S.C. 154(b), the term of this patent shall be extended for 0 days.

(21) Appl. No.: 09/410,341

(22) Filed: Sep. 30, 1999

(51) Int. Cl.[7] ............................... C12Q 1/00; C12Q 1/04; C12Q 1/06; C12M 1/00; A01K 43/00

(52) U.S. Cl. ................................. 435/4; 435/7.9; 435/7.1; 435/39; 435/34; 435/31; 435/817; 435/283.1; 435/286.5; 435/287.1; 435/287.4; 426/231

(58) Field of Search ................................. 435/4, 7.9, 7.1, 435/39, 34, 31, 817, 283.1, 286.5, 287.1, 287.4; 426/231

(56) References Cited

U.S. PATENT DOCUMENTS 5,976,896 * 11/1999 Kumar et al. ............................ 435/4
6,051,388 * 4/2000 Bodenhamer ....................... 435/7.32

* cited by examiner

Primary Examiner—Louise N. Leary
(74) Attorney, Agent, or Firm—Calvin B. Ward

(57) ABSTRACT

The present invention is a disposable element for assaying food samples and a method for using the element. The disposable element includes a container having first, second, and third ports, a prefilter disposed in the container, an immuno-sorbent layer having antibodies to a target microbe affixed thereto, the immuno-sorbent layer also being disposed in the container, and an electrode in contact with the immuno-sorbent layer. The prefilter and immuno-sorbent layers are positioned in the container such that a sample introduced into the first port passes through the prefilter and the immuno-sorbent layer when a pressure differential is created between the first and third ports. In addition, liquid entering the second port passes through the immuno-sorbent layer, but not the prefilter, when a pressure differential is created between the second and third ports. The prefilter preferably has a pore size between 10 and 30 microns. The disposable element may be used to measure the level of microbiological contamination in a solid sample caused by a predetermined microbe. The sample is pretreated by mixing the sample with a buffer solution and blending buffer and sample. An aliquot of the blended sample is introduced into the disposable element and is filtered through the prefilter and then passes through the immuno-sorbent layer. A solution having labeled antibodies to the microbe is passed through the immuno-sorbent layer via the second port and the amount of label bound to the immuno-sorbent is measured.

5 Claims, 1 Drawing Sheet

APPARATUS FOR DETECTING CONTAMINATION IN FOOD PRODUCTS

FIELD OF THE INVENTION

This invention relates to sensors for detecting and quantifying a target microorganism in food products and more particularly to a flow-through disposable sensor.

BACKGROUND OF THE INVENTION

The centralization of food processing in large plants supplying millions of pounds of food products has aggravated the problems associated with microbial contamination of the products. When a production line becomes contaminated, the health of large numbers of people is threatened. In addition, the centralization of processing increases the time period between the processing of the food product and the final consumption of that product. Since bacteria continue to grow during this time period, a marginally contaminated product can become unfit for consumption by the time it reaches the consumer.

Accordingly, there is an increasing need for systems that detect contamination at the plant in time to prevent shipment of a contaminated product. Ideally, such a system would detect contamination in time to shut down a production line before large quantities of product are contaminated. Since bacteria can grow rapidly on food products such as ground meat, such an assay system must be able to detect contamination at very low levels, typically 100 to 1000 bacteria per gram of ground meat.

Assay systems that can quickly detect microorganisms based on immunological techniques have been known for some time. Immunoassay techniques are based on the ability of antibodies to form complexes with the corresponding antigens. This property of highly specific molecular recognition of antigens by antibodies leads to high selectivity of assays based on immune principles. The high affinity of antigen-antibody interactions allows very small quantities of microorganisms to be determined. In addition, microorganisms are typically classified according to the antigens on the organism's surface; hence, immunological assays also yield results that provide the identity of the contaminating organism as well as the level of contamination.

Immunoassay techniques are used mainly in clinical analyses and medical diagnostics. Immunoassay techniques could, in principle, be utilized in many non-clinical applications if assay systems that were better adapted for field operating conditions were available. Conventional immunoassay techniques (such as ELISA, immunoblot, immunoagglutination) can be used only in specially equipped laboratories and require technically trained personnel. These assays are difficult to conduct in the non-laboratory conditions typically encountered in field settings or food processing lines.

During the last few years, a significant number of publications have dealt with alternative immunoassay techniques. The development of alternative immunoassay techniques aims in most cases at improvements in performance of conventional immuno-analysis to decrease the analysis time, increase assay sensitivity, and simplify and automate assay procedures. The basic principles of the alternative immunoassay methods are the same as for conventional immunoassay techniques in that these alternative assays are also based on the detection of antigen-antibody interaction. Frequently the term 'biosensor' or 'immunosensor' is used to label an immunoassay system that is an alternative to a conventional assay system, developed with automated data acquisition.

In general, an immuno-sensor (biosensor) consists of a signal transducer and a biochemically interactive system employing principles of biological molecular recognition. Based on the nature of the physical detection used in the transducer, immuno-sensing systems can be classified as optical, gravimetric and electrochemical. In optical transducers, detection is based on light-sensitive elements. The optical signal detection can be conducted by spectrophotometric, spectrofluorimetric, hemiluminometric, reflectometric or other related techniques.

Gravimetric transducers are based on sensitive detection of mass changes following antigen-antibody complex formation. Piezoelectric detectors are typically based on acoustical resonators having resonant frequencies that are altered by the change in mass of a layer which is in contact with the resonator. This layer typically includes one member of an antigen-antibody complex. When the other member attaches to the layer, the resonance frequency shifts. These transducers cannot distinguish between specific binding and non-specific binding.

Electrochemical transducers are based on detection of changes in electro transfer caused by the immuno-interaction. In particular, this detection is brought about using amperometric, poteniometric, conductometric (at constant voltage) or impedimetric (at alternative voltage) devices.

Flow-injection principles can be used to enhance the efficiency of the immuno-interaction. Prior art flow-injection immuno-sensing systems are based on a principle of displacement. In this case, the immunoassay system is arranged as a column containing immobilized antibodies. The column is saturated with a solution containing a labeled antigen. After antigen-antibody interaction has occurred, the column contains a solid carrier with immobilized antibody-labeled antigen complexes. The affinity of antibodies for labeled antigens is usually significantly lower than their affinity for unlabeled (free) antigen due to stearic factors. Therefore, injection of free antigen into the column results in displacement of the labeled antigen by the unlabeled antigen. Labeled antigen is then detected at the outlet of the column. A similar scheme can be realized based on the use of immobilized antigen. In this case, injection of the analyte leads to replacement of the antibody-conjugated complex. Flow-injection immunoassay systems based on displacement schemes for real time (two-three minutes) determination of a number haptens have been reported by Liegler, et al. in U.S. Pat. No. 5,183,740. However, these flow-injection schemes have substantially less sensitivity than the conventional assay systems.

Traditional immuno-analysis schemes (competitive binding and 'sandwich' schemes) are also employed in flow-injection immunoassay systems. In these cases, the problem of column regeneration is an important issue. The problem associated with the necessity to renew the immuno-sorbent in flow-injection systems can be solved by development of disposable immuno-columns. While such sensors solve the problems associated with disposability in a clinical laboratory setting, these sensors are less than optimal in the food production line setting in which multiple infective agent assays must be performed on samples that include biological material that clogs the sensors and exhibit non-specific binding for the sensor material.

Broadly, it is the object of the present invention to provide an improved immunoassay apparatus.

It is a further object of the present invention to provide a disposable flow-immunoassay apparatus that is adapted for use in the food processing environment.

It is yet another object of the present invention to provide an assay system that can simultaneously detect multiple infective agents.

These and other objects of the present invention will become apparent to those skilled in the art from the following detailed description of the invention and the accompanying drawings.

SUMMARY OF THE INVENTION

The present invention is a disposable element for assaying food samples and a method for using the element. The disposable element includes a container having first, second, and third ports, a prefilter disposed in the container, an immuno-sorbent layer having antibodies to a target microbe affixed thereto, the immuno-sorbent layer also being disposed in the container, and an electrode in contact with the immuno-sorbent layer. The prefilter and immuno-sorbent layers are positioned in the container such that a sample introduced into the first port passes through the prefilter and the immuno-sorbent layer when a pressure differential is created between the first and third ports. In addition, liquid entering the second port passes through the immuno-sorbent layer, but not the prefilter when a pressure differential is created between the second and third ports. The prefilter preferably has a pore size between 10 and 30 microns. The disposable element may be used to measure the level of microbiological contamination in a solid sample caused by a predetermined microbe. The sample is pretreated by mixing the sample with a buffer solution and blending buffer and sample. An aliquot of the blended sample is introduced into the disposable element and is filtered through the prefilter and then passes through the immuno-sorbent layer. A solution having labeled antibodies to the microbe is passed through the immuno-sorbent layer via the second port and the amount of label bound to the immuno-sorbent layer is measured.

DETAILED DESCRIPTION OF THE INVENTION

Figure 1:
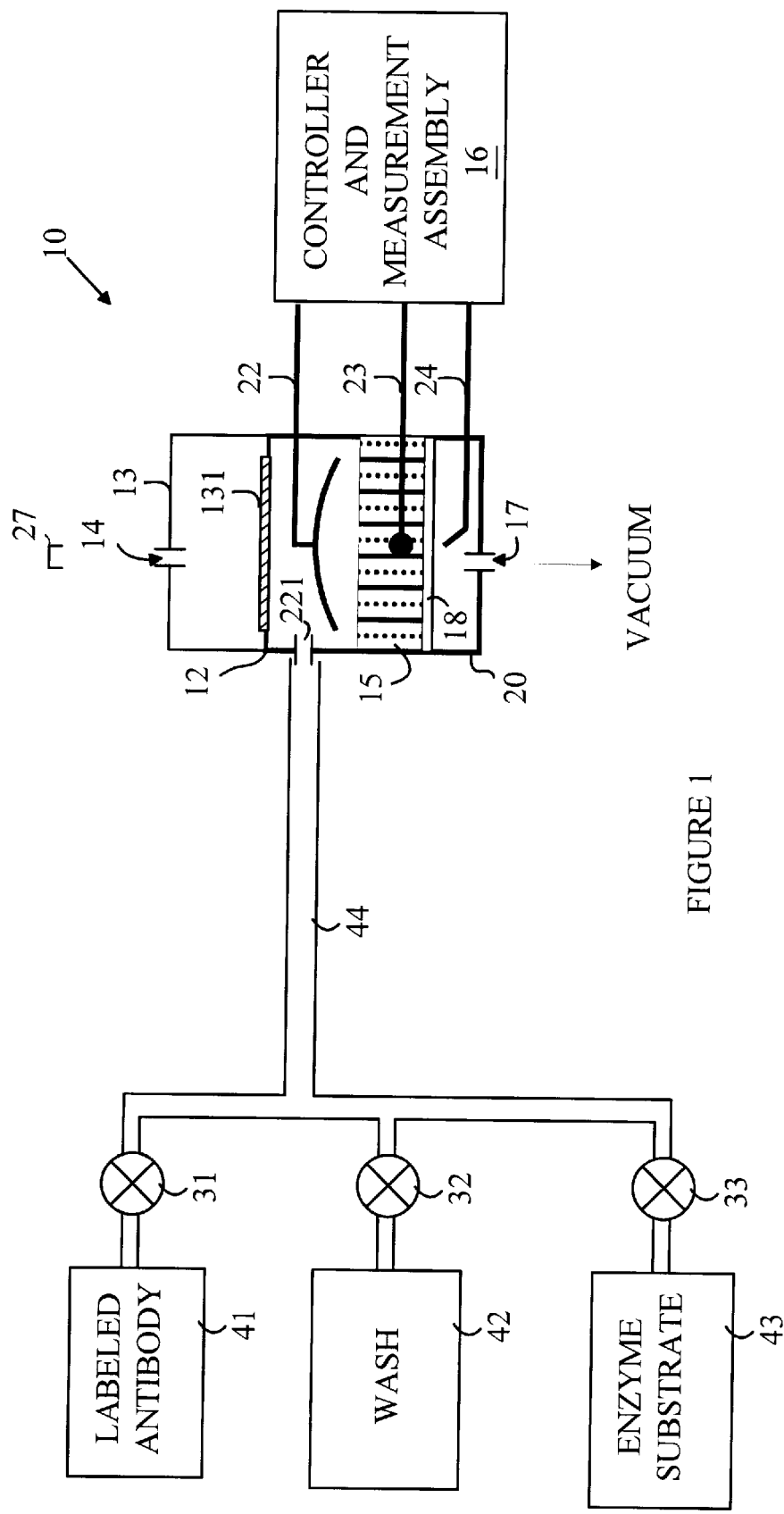
FIG. 1 is a schematic drawing of a flow-through sensor system according to the present invention.

The present invention may be more easily understood with reference to the standardized sample preparation and testing utilized in detecting micro-organisms in solid food products such as hamburger. In general, a sample of the hamburger is removed from the food processing line and blended with a buffer solution. The blended meat/buffer solution is then filtered to remove large particulate matter. The filtrate is then tested for specific micro-organisms. Ideally, the test should yield results in a matter of minutes, since the food production line is still running while the samples are being analyzed. If the line is contaminated, all of the material being processed will need to be diverted to other products such as pet food or thrown out. Hence, shorter detection times reduce the amount of material that is lost to contamination when the processing equipment becomes contaminated.

The present invention may be more easily understood with reference to an assay according to the present invention for detecting $E.$ $Coli$ contamination in meat products. The meat sample is first blended with a buffer to free the contaminating microbes. In the preferred embodiment of the present invention, the meat sample is placed in a stomacher bag (25 g sample and 225 ml phosphate buffer pH 5.6 containing 0.15M NaCl and 0.01% Tween 20) which is placed in a Stomacher and stomached for 2 minutes at the normal speed. The extracted solution is filtered through Whatman No. 1 filter membrane using a Buchner Funnel connected to a vacuum line. A maximum of 5 ml of solution is filtered through the Whatman filter. If more material is needed, a new filter is utilized. This prefiltration step removes the majority of the large particles and results in a semi-clear solution containing no more than 5% fat globules.

One 1 ml of filtered solution is drawn through a sensing element having an immuno-sorbent layer that contains antibodies to $E.$ $coli$. If $E.$ $coli$ are present in the filtrate, the micro-organisms are bound to the immuno-sorbent by the antibodies attached to the particles. A second solution containing an antibody to a different antigen on the surface of the target micro-organism is then introduced into the immuno-sorbent. These antibodies are labeled with an enzyme that catalyzes a reaction involving a substrate Y. After a predetermined quantity of the labeled antibody has passed through the immuno-sorbent layer, the immuno-sorbent is washed with carrier liquid. A solution containing substrate Y is then introduced into the immuno-sorbent. Simultaneously, the amperometric output from electrodes that measure the conversion of Y in the immuno-sorbent layer is measured. The amperometric output is proportional to the concentration of the product of enzymatic reaction and therefore, proportional to the amount of the enzyme label bound to the immuno-sorbent. The bound concentration of bound enzyme is proportional to the number of $E.$ $coli$ bound to the immuno-sorbent.

The present invention is based on the observation that there is an optimal range of filter pore sizes for the filters used to remove the particulate matter from the blended meat or other products. If a filter with too large a pore size is used, fat globules and other debris that nonspecifically bind to the bio-sensor reach the bio-sensor. If the filter has pores that are too small, organisms of interest will be lost in the filter, and the bacterial count may be under estimated. In addition, the amount of material that is filtered must be carefully controlled to avoid a build-up of material on the filter surface. Such a build up can also trap organisms of interest.

It has been found experimentally that a pore size in the 10–30 micron range provides satisfactory results. The preferred embodiment of the present invention utilizes a #1 Whatman filter with a pore size of 11 microns. This arrangement allows approximately 50 percent of the micro-organisms present to pass through the prefilter while providing a background that is sufficiently low to allow the detection of less than 300 $E.$ $coli$/gm of meat.

In the preferred embodiment of the present invention, the pre-filtration filter and immuno-sorbent layer are combined into a single disposable element that can be connected to a measurement assembly and the appropriate fluid reservoirs. Refer now to FIG. 1, which is a cross-sectional view of a measurement system 10 consisting of a disposable detection module 12 connected to a measurement and control assembly 16. Disposable module 12 includes a prefilter assembly 13 having the Whatman filter 131 described above mounted therein. The blended sample is introduced through a first port 14. The material is drawn through the filter 131 and then into a detector module 20. Detector module 20 includes an immuno-column 15, which is preferably constructed from a highly dispersed conducting material such as carbon to which antibodies have been absorbed or covalently bound.

Immuno-column 15 serves as both an immuno-reactor and an electrochemical measuring cell. Immuno-column 15 is preferably deposited on the filter membrane 18. Filter membrane 18 is preferably constructed from glass, paper, or plastic. Embodiments of the present invention in which the antibodies are directly absorbed onto filter membrane 18 without the use of the dispersed material described above may also be constructed.

The manner in which the system shown in FIG. 1 is used to measure the concentration of micro-organisms may be more easily understood with reference to performing a conventional 'sandwich' immuno-analysis for a target analyte, X, which in this case is the target micro-organism. The immuno-sorbent layer is assumed to be loaded with antibodies to X which are immobilized on the immuno-sorbent at the start of the assay.

Disposable element 12 is first connected to controller 16 and a manifold 44. The connection to manifold 44 can be made by connecting elastic tubing over port 221. In the preferred embodiment of the present invention, manifold 44 includes the elastic tubing. Port 17 is likewise connected via elastic tubing to a vacuum line. Electrodes 22–24 are preferably connected to controller 16 via a snap-on connector.

The sample is injected into immuno-column 15 by causing a sample of the filtrate from the food sample to pass through the immuno-column by injecting the sample into prefilter unit 13 via port 14. After passing through prefilter 131, the filtered sample passes through immuno-column 15. During this filtration process, port 221 is either blocked or sufficient vacuum must be utilized to overcome leakage through port 221. In the preferred embodiment of the present invention, valves 31–33, which connect port 221 to reservoirs 41–43 containing the various solutions discussed below block port 221 during the filtration process. These valves are under the control of controller 16 which preferably includes a micro-processor that is programmed to perform the various control functions and provide instructions to the operator.

If micro-organisms having X on their surface are present in the filtrate, the micro-organisms are bound to the immuno-sorbent by the antibodies attached to the particles. A second solution containing an antibody to a different antigen on the surface of the target micro-organism is then introduced from a reservoir 41 into the immuno-column via port 221 after blocking port 14. These antibodies are labeled with an enzyme that catalyzes a reaction involving a substrate Y. After a predetermined quantity of the labeled antibody has passed through the immuno-column, the immuno-column is washed with carrier liquid that is also introduced via port 221 from a reservoir 42. A solution containing substrate Y is then introduced into immuno-column 15 via port 221 from a reservoir 43. Simultaneously, the amperometric output from electrodes 22–24 is measured by assembly 16. The output is the current generated between the working and counter electrodes, shown at 23 and 22, respectively, when the potential between the working electrode and reference electrode 24 is maintained at a constant value. The electrodes are included in disposable element 12. The amperometric output is proportional to the concentration of the product of enzymatic reaction and therefore, proportional to the amount of the enzyme label bound to the immuno-sorbent layer. The bound concentration of bound enzyme is proportional to the number of micro-organisms bound to the column.

As noted above, after the prefiltration is complete, port 14 must be blocked sufficiently so that air entering the port does not interfere with the dispensing of solutions from the various reservoirs. A disposable cap 27 can be provided for this port. The cap is placed over the port after the sample has passed through filter 131. However, if port 14 is sufficiently small, the air leakage through this port will not be sufficient to interfere with dispensing operations. In addition, it should be noted that the material trapped on filter 131 also tends to block the flow of air from port 14 into detector module 20.

The above-described embodiments of the present invention have utilized a reference electrode and a counter electrode that are part of the disposable element. However, an arrangement in which the counter electrode is placed in manifold 44 and the reference electrode is placed in the vacuum line just after port 17 may also be practiced. Such embodiments simplify the disposable element; however, such embodiments require additional maintenance to assure that the electrodes are clean.

The above-described embodiments of the present invention have utilized solid food samples such as meat. However, the present invention can be applied to other food samples such as milk. In the case of milk or other liquid samples, the blending step discussed above can be omitted.

Various modifications to the present invention will become apparent to those skilled in the art from the foregoing description and accompanying drawings. Accordingly, the present invention is to be limited solely by the scope of the following claims.

What is claimed is:

1. A method for measuring the level of microbiological contamination in a food sample caused by a predetermined microbe, said method comprising the steps of:

mixing said sample with a buffer solution introducing an aliquot of sample mixture into a disposable element;

filtering said aliquot of said sample through a filter paper having a pore size between 10 and 30 microns;

passing said filtered aliquot through an immuno-sorbent layer having antibodies that bind said microbe;

passing a solution having labeled antibodies to said microbe through said immuno-sorbent layer;

measuring the amount of label bound to said immuno-sorbent layer.

2. The method of claim 1 further comprising the step of blending said sample prior to filtering said sample through said filter paper.

3. The method of claim 1 wherein said labeled antibodies are labeled with an enzyme that catalyzes a reaction involving a substrate Y and wherein said measurement step comprises causing a solution containing Y to flow through said immuno-sorbent layer and measuring the electrical output of a first electrode in contact with said immuno-sorbent layer and a second electrode in contact with liquid flowing through the immuno-sorbent layer.

4. A disposable element for assaying food samples, said disposable element comprising:

a container having first, second, and third ports;

a prefilter disposed in said container;

an immuno-sorbent layer having antibodies to a target microbe affixed thereto, said immuno-sorbent layer being disposed in said container; and an electrode in contact with said immuno-sorbent layer, wherein said prefilter and said immuno-sorbent layer are positioned in said container such that a sample introduced into said first port passes through said prefilter and said immuno-sorbent layer when a pressure differential is created between said first and third ports and wherein liquid entering said second port passes through said immuno-sorbent layer, but not said prefilter, when a pressure differential is created between said second and third ports.

5. The disposable element of claim 4 wherein said prefilter has a pore size between 10 and 30 microns.

* * * * *